United States Patent [19]
Matsutani et al.

[11] Patent Number: 5,552,427
[45] Date of Patent: Sep. 3, 1996

[54] GLUTAMINASE INHIBITORY COMPOUNDS, COMPOSITIONS, AND METHODS OF USE

[75] Inventors: Etsuya Matsutani; Shogo Marui, both of Kobe, Japan

[73] Assignee: Takeda Chemical Industries, Ltd., Osaka, Japan

[21] Appl. No.: 345,425

[22] Filed: Nov. 21, 1994

[30] Foreign Application Priority Data

Nov. 19, 1993 [JP] Japan ................................ 5-290278

[51] Int. Cl.⁶ ................ C07D 233/64; C07D 233/20; A61K 31/415
[52] U.S. Cl. ................ 514/398; 548/331.5; 548/332.1; 548/332.5; 548/335.1; 548/347.1
[58] Field of Search ................ 548/331.5, 332.1, 548/335.1, 347.1, 332.5; 514/398

[56] References Cited

U.S. PATENT DOCUMENTS

| | | | |
|---|---|---|---|
| 2,742,481 | 4/1956 | Cain | 548/331.5 |
| 3,459,763 | 8/1969 | Gruenfeld | 548/331.5 |
| 4,801,602 | 1/1989 | Ahond et al. | 514/398 |

FOREIGN PATENT DOCUMENTS

| | | | |
|---|---|---|---|
| 0550697 | 12/1957 | Canada | 548/331.5 |
| 0215687 | 3/1987 | European Pat. Off. | 548/331.5 |
| 0397567 | 11/1990 | European Pat. Off. | 548/331.5 |
| 0403318 | 12/1990 | European Pat. Off. | 548/331.5 |
| 1458811 | 11/1966 | France | 548/331.5 |
| 2585020 | 1/1987 | France | 514/398 |
| 2681323 | 3/1993 | France | 548/331.5 |
| 2600537 | 7/1976 | Germany | 548/331.5 |
| 1132013 | 10/1968 | United Kingdom | 548/331.5 |

OTHER PUBLICATIONS

Colson et al., "Mode of Action of the Antitumor Compound Girodazole (RP 49532A, NSC 627434)", Biochem. Pharm., vol. 43, No. 8, (1992), pp. 1717–1723.

Cook et al., "Studies on the Toxic Effects of Some Nitrogen-Containing Secondary Plant Compounds on Rat Hepatoma Cells", vol. 14, May 1986, pp. 1053–1054.

Lillie et al., "Cyclocreatine (1–Carboxymethyl–2–iminoimidazolidine) Inhibits Growth of a Broad Spectrum of Cancer Cells Derived from Solid Tumors", Cancer Research, vol. 53, No. 13, Jul. 1993, pp. 2937–3215.

Mulcahy et al., "Enhancement Of Melphalan (L–PAM) Toxicity By Reductive Metabolites Of 1–Methyl–2–Nitroimidazole, A Model Nitroimidazole Chemosensitizing Agent", *Biochemical Pharmacology*, vol. 40, No1 12, pp. 2671–2676, (1990).

*Primary Examiner*—Floyd D. Higel
*Attorney, Agent, or Firm*—Foley & Lardner

[57] ABSTRACT

There is disclosed a pharmaceutical composition for inhibiting glutaminase which comprises a imidazole derivative or a salt thereof. This compound selectively inhibits the proliferation of tumor cells, and the composition is useful as an anti-cancer agent. There is also disclosed a imidazole derivative having glutaminase inhibitory activity.

18 Claims, No Drawings

GLUTAMINASE INHIBITORY COMPOUNDS, COMPOSITIONS, AND METHODS OF USE

FIELD OF THE INVENTION

The present invention relates to a glutaminase inhibitor comprising an imidazole compound as an active ingredient. Specifically, it relates to a pharmaceutical composition inhibiting the proliferation of malignant tumors originated mainly in the large intestine, malignant tumors derived therefrom and distantly metastasized to organs such as the liver, and malignant tumors originated in the stomach, prostate gland, liver, etc., by inhibiting the enzyme glutaminase (EC 3.5.1.2) in mitochondrial membranes of the tumor cells.

BACKGROUND OF THE INVENTION

The enzyme glutaminase in the membranes of mitochondria, i.e., organelles producing energy of cells, is known as one of the enzymes that are characteristically required for the proliferation of some tumor cells and utilized only in a trace amount in other normal cells. Researchers have not succeeded in developing clinically satisfactory anti-cancer agents that, by inhibiting this enzyme, selectively inhibit the proliferation of tumor cells and cause no damage to other cells (e.g., Medina et al., "Miguel Angel Medina": Molecular and Cellular Biochemistry, 113, 1–15 (1992)).

The number of patients with a large intestinal cancer (e.g., colon carcinoma, rectum carcinoma) is the largest next to that of patients with lung carcinoma, and the large intestinal cancer has a high postoperative recurrence rate. At present, there is no postoperative auxiliary chemotherapeutic agent that is effective alone. Combinations of conventional chemotherapeutic agents, e.g., mainly the antimetabolite 5-fluorouracil (5-FU), have been used for the therapy. However, effective standard therapies against the disease have not been established yet (see e.g., "Carcinoma of the Colon and Rectum", Medical View, 1989). Novel selective therapeutic agents against large intestinal cancers are being developed all over the world. However, clinically effective ones have not developed yet (e.g., Colon Cancer Cells, p.1, M. P. Moyer and G. H. Poste ed., Academic Press, Inc., (1990)).

The following compounds are known.

(1) The compound (A) described in Cancer Research, 53, 3172–3178, Jul. 1, 1993:

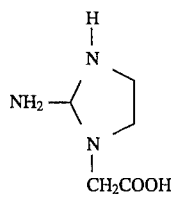
(A)

(2) The compound (B) described in JP-A 62-7732, JP-A 3-17064, Biochemical Pharmacology, Vol. 43, No. 8, pp. 1717–1723, 1992:

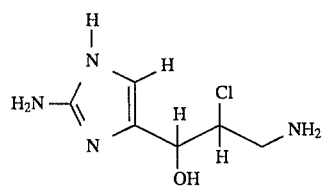
(B)

(3) The compound (C) described in JP-A 3-5461:

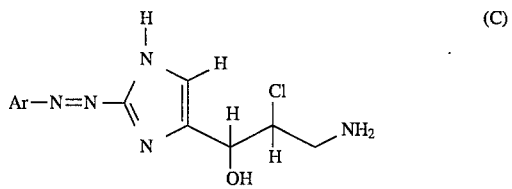
(C)

Ar=phenyl, alkyl, etc.

(4) The compound (D) described in FR-2681323-A1:

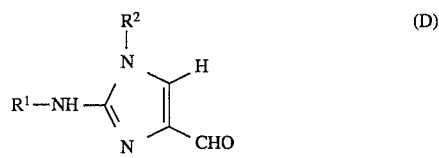
(D)

$R^1$, $R^2$=optionally protected amino (5) The compound (E) described in Biochemical Society Transactions, 14, 1053–1054, 1986:

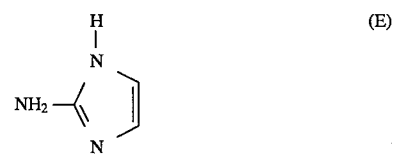
(E)

The above compounds (A), (B), (C) and (D) have different chemical structures and action mechanisms from those of the compound in the present invention. There is no description that the compound (E) inhibits glutaminase and selectively inhibits the proliferation of tumor cells.

Thus, there is a need for highly selective therapeutic agents that have potent inhibitory activity against the proliferation of tumor cells and have no toxicity to normal in vivo tissues.

OBJECTS OF THE INVENTION

The main object of the present invention is to provide a pharmaceutical composition for inhibiting glutaminase.

Another object of the present invention is to provide a glutaminase inhibitory composition.

Still another object of the present invention is to provide a novel imidazole derivative having glutaminase inhibitory activity.

These objects as well as other objects and advantages of the present invention will become apparent to those skilled in the art from the following description.

SUMMARY OF THE INVENTION

In order to achieve the above objects, the present inventors have made intensive screening studies on compounds selectively inhibiting the proliferation of human colonic or rectal carcinoma cell strains. As a result, it has been found that certain imidazole derivatives specifically inhibit the activity of the mitochondrial enzyme glutaminase of human colonic or rectal carcinoma cells and exhibit highly selective inhibitory activity against the proliferation of large intestinal cancer cells. After further studies based on these findings, the present invention has been completed.

The present invention provides a pharmaceutical composition for inhibiting glutaminase which comprises a compound of the formula (I):

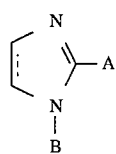

(I)

wherein A is an optionally substituted lower alkyl group or an optionally protected amino group, ---- is a single bond or a double bond, and B is a hydrogen atom or an optionally substituted chain hydrocarbon group, or a salt thereof, and a pharmaceutically acceptable carrier or excipient.

The present invention also provides a glutaminase inhibitory composition which comprises a compound of the formula (I).

The present invention also provides a compound of the formula (II):

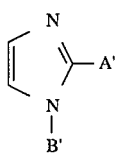

(II)

wherein A' is an amino group optionally protected with an acyl group, B' is an optionally substituted chain hydrocarbon group; provided that, when B' is methyl or ethyl, A' is an amino group protected with an acyl group; or a salt thereof.

DETAILED DESCRIPTION OF THE INVENTION

In the above formulas, A is an optionally substituted lower alkyl group or an optionally protected amino group.

Examples of the lower alkyl group represented by A include straight-chain or branched alkyl groups having 1 to 6 carbon atoms such as methyl, ethyl, propyl, isopropyl, butyl, isobutyl, pentyl, hexyl, etc. Preferred examples thereof are straight-chain or branched chain alkyl groups having 1 to 3 carbon atoms such as methyl, ethyl, etc.

Each of these lower alkyl groups may optionally be substituent with 1 to 3 substituents selected from hydroxy, amino, carboxyl, nitro, mono- or di-$C_{1-6}$ alkylamino (e.g., methylamino, ethylamino, propylamino, dimethylamino, diethylamino, etc.), $C_{1-6}$ alkoxy (e.g., methoxy, ethoxy, propoxy, hexyloxy, etc.), $C_{1-6}$ alkyl-carbonyloxy (e.g., acetoxy, ethylcarbonyloxy, etc.) and halogen (e.g., fluorine, chlorine, bromine, iodine, etc.).

The optionally protected amino group represented by A include an amino group and a protected amino group. The protective group of the protected amino group is a group removable by in vivo metabolism. Examples of the protective group include an acyl group and an optionally substituted alkylidene group. When the protective group is an optionally substituted alkylidene group, the amino group of the optionally protected amino group forms Schiff base.

Examples of the acyl group as the protective group include straight-chain or branched $C_{1-6}$ alkanoyl groups optionally containing an unsaturated bond (e.g., formyl, acetyl, propionyl, butyryl, isobutyryl, valeryl, isovaleryl, pivaloyl, hexanoyl, acryloyl, methacryloyl, crotonoyl, isocrotonoyl, propioloyl, etc.), $C_{6-10}$ aroyl groups (e.g., benzoyl, 1-naphthoyl, 2-naphthoyl, etc.), $C_{1-3}$ alkylsulfonyl groups (e.g., methanesulfonyl, ethanesulfonyl, etc.), $C_{6-10}$ arylsulfonyl (e.g., benzenesulfonyl, p-toluenesulfonyl, 1-naphthalenesulfonyl, 2-naphthalenesulfonyl, etc.), —COOR wherein R is a lower alkyl group or benzyl group, and —CONR$^1$R$^2$ wherein R$^1$1 and R$^2$ are the same or different and are a hydrogen atom, lower alkyl group or aryl group. The lower alkyl group represented by R, R$^1$1 or R$^2$ is as defined for the lower alkyl group represented by A. Examples of the aryl group represented by R$^1$ and R$^2$ include $C_{6-10}$ aryl groups such as phenyl, 1-naphthyl and 2-naphthyl.

Examples of the optionally substituted alkylidene group as the protective group include ethylidene, isopropylidene, benzylidene, p-nitrobenzylidene, salicylidene, dimethylaminomethylene, etc.

When the alkyliden group is substituted, examples of the substituent are a $C_{1-6}$ alkylthio group (e.g., methylthio, ethylthio, propylthio, etc.), a mono- or di-$C_{1-6}$ alkylamino (e.g., methylamino, ethylamino, dimethylamino, diethylamino, etc.), a $C_{1-6}$ alkoxy group (e.g., methoxy, ethoxy, propoxy, etc.), a halogen (e.g., fluoro, chloro, bromo, etc.), a hydroxyl group, a nitro group and so on.

The protective group is preferably an acyl group, more preferably —COOR wherein R is as defined above, particularly preferably —COOR wherein R is a benzyl group.

These protective groups can be introduced by per se known methods (T. W. Green and P. G. M. Wuts, "Protective groups in Organic Synthesis", 2ed., John Wiley & Sons, Inc., New York (1991)).

---- is a single bond or double bond, and preferably a double bond.

B is a hydrogen atom or an optionally substituted chain hydrocarbon group.

Examples of the chain hydrocarbon group represented by B include lower alkyl groups, lower alkenyl groups, lower alkynyl groups, etc. Preferred examples thereof are lower alkyl groups.

The lower alkyl groups for B are as defined for the lower alkyl groups for A. In particular, a methyl group is preferred.

Examples of the lower alkenyl group for B include straight-chain or branched alkenyl groups having 2 to 6 carbon atoms such as vinyl, allyl, isopropenyl, 2-methallyl, 3-methallyl, 3-butenyl, etc. In particular, an allyl group is preferred.

Examples of the lower alkynyl group for B include straight-chain or branched alkynyl groups having 2 to 6 carbon atoms such as ethynyl, 2-propinyl, 3-hexynyl, etc. In particular, a 2-propynyl group is preferred.

Each of these chain hydrocarbon groups represented by B may optionally be substituted with 1 to 3 substituents selected from those of the above lower alkyl group represented by A.

A is preferably an amino group or a protected amino group such as benzyloxycarbonylamino, etc. In particular, an amino group is preferred.

B is preferably a $C_{1-3}$ alkyl group such as methyl.

The compound of the formula (I) may be a compound of the formula (II):

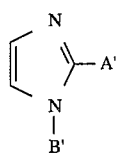

(II)

wherein A' is an amino group optionally substituted with an acyl group, B' is an optionally substituted chain hydrocarbon group; provided that, when B' is methyl or ethyl, A' is an amino group protected with an acyl group; or a salt thereof.

The acyl group as the protective group for A' is as defined for that for A. The optionally substituted chain hydrocarbon group represented by B' is as defined for that represented by B.

A' is preferably an amino group protected with an acyl group, more preferably —NHCOOR wherein R is a lower alkyl group as defined for A or a benzyl group. In particular, A' is preferably benzyloxycarbonylamino.

B' is preferably a lower alkyl group as defined for A, more preferably a methyl group.

The compound of the formula (I) or (II) is preferably 2-amino-1-methylimidazole or 2-benzyloxycarbonylamino-1-methylimidazole, or a salt thereof.

Regardless of the kind of substituent represented by A, B, A' or B' in the formulas, the compound of the formula (I) or (II) may be reacted with an acid to form a salt. Examples of the acid include organic acids (e.g., acetic acid, ethylsuccinic acid, ethylcarbonic acid, glycopeptonic acid, stearic acid, propionic acid, lactobionic acid, oxalic acid, maleic acid, fumaric acid, succinic acid, lactic acid, trifluoroacetic acid, methanesulfonic acid, p-toluenesulfonic acid, benzenesulfonic acid, etc.) and mineral acids (e.g., hydrochloric acid, sulfuric acid, nitric acid, phosphoric acid, hydroiodic acid, etc.). Preferred examples the acid are acetic acid, stearic acid, oxalic acid, succinic acid, lactic acid, hydrochloric acid, sulfuric acid, nitric acid, etc. More preferred examples thereof are acetic acid and hydrochloric acid.

When ---- represents a single bond, the compound of the formula (I) can convert to its tautomer. When the tautomer forms, the compound of the formula (I) may exist as their mixtures.

The compound of the formula (I) or a salt thereof can be prepared by per se known methods or modifications thereof. For example, they can be prepared by the method described in J. Chem. Soc. p. 307 (1956) or Khim. Geterotsikl. Soedin., p. 180 (1969) or modifications thereof.

For example, 1-alkyl-2-aminoimidazole derivative (IV) can be prepared by the cyclization reaction of guanidine derivative (III) in the presence of an acid catalyst. 1 -Alkylimidazole derivative (VI) can be prepared by the alkylation reaction of compound (V). When A is a protected amino group, compound (III) can also be prepared by the deprotection of compound (VI). Protective groups can be introduced to compound (IV) on the contrary.

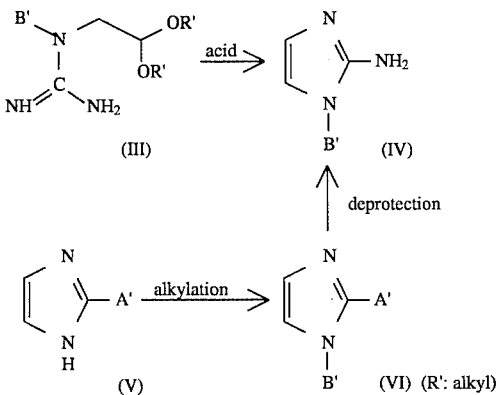

Imidazoline derivatives represented by the formula (I) wherein ---- is a single bond can be prepared by per se known methods or modifications thereof. For example, they can be prepared by the method described in J. Org. Chem., 24, p. 1157 (1959), or by performing a hydrogenation reaction to a final product or an intermediate of the preparation of (IV)–(VI).

The compound (I) or its salt has potent and selective inhibitory activity against the proliferation of tumor cells and can safely be used in mammals such as humans, mice, etc. In particular, it is useful as a pharmaceutical composition for treating malignant tumors originated in the large intestine, and malignant tumors derived from the large intestinal malignant tumors and distantly metastasized to organs such as the liver, etc.

The compound (I) or its salt may be administered as its bulk, but normally as dosage forms prepared by conventional methods, for example, by mixing the compound (I) or its salt with a suitable amount of a pharmaceutically acceptable carrier such as excipients (e.g., calcium carbonate, kaolin, sodium bicarbonate, lactose, starches, crystalline cellulose, talc, fine granulated sugar, porous materials, etc.), binders (e.g., dextrin, gums, α-starch, gelatin, hydroxypropylcellulose, hydroxypropylmethylcellulose, pullulan, etc.), disintegrators (e.g., carboxymethylcellulose calcium, croscarmellose sodium, crospovidone, low substituted hydroxypropylcellulose, starch partially in the α-form, etc.), lubricants (e.g., magnesium stearate, calcium stearate, talc, starch, sodium benzoate, etc.), colorants (e.g., tar color, caramel, iron sesquioxide, titanium oxide, riboflavins, etc.), corrigents (e.g., sweetening agents, flavoring agents, etc.), stabilizers (e.g., sodium sulfite, etc.), preservatives (e.g., parabens, sorbic acid, etc.), etc.

The pharmaceutical composition of the present invention contains a therapeutically effective amount of the compound (I) or a salt thereof. The content of the compound (I) or a salt thereof in the composition of the present invention is normally 0.1 to 100% by weight, preferably 5 to 50% by weight, based on the total weight of the composition.

Examples of dosage forms include tablets including sugar-coated tablets and film-coated tablets, pills, capsules, granules, fine granules, powders, syrups, emulsions, suspensions, injections, etc. These preparations can be prepared by conventional methods such as the methods described in Japanese Pharmacopoeia.

Specifically, tablets can be prepared by granulating the compound (I) or a salt thereof as it is, or granulating a homogeneous mixture of it with an excipient, binder disintegrator or other appropriate additives according to a suitable method, then adding a lubricant, etc., and compressing the mixture for shaping. Alternatively, tablets can directly be prepared by compressing the compound (I) or a salt thereof as it is or a homogeneous mixture of it with an excipient, binder, disintegrator or other appropriate additives. Furthermore, tablets can also be prepared by compressing granules per se prepared in advance or a homogeneous mixture of it with an appropriate additive. If necessary, the composition may contain a colorant, corrigent, etc. Further, the composition may be coated with an appropriate coating agent.

Injections can be prepared by charging a container with a suitable amount of the compound (I) or a salt thereof, or a suitable amount of a solution, suspension or emulsion of it in water for injection, physiological saline, Ringer's solution in the case of using an aqueous solvent, or a suitable amount of a solution, suspension or emulsion of it normally in vegetable oils in the case of using a nonaqueous solvent, and then sealing the container.

Examples of the carriers for oral compositions include materials conventionally used in pharmaceutics such as starch, mannit, crystalline cellulose, carboxymethylcellulose, etc. Examples of the carriers for injections include distilled water, physiological saline, glucose solution, transfusion solution, etc. In addition, additives generally used in pharmaceutics can appropriately be added.

The pharmaceutical composition of the present invention selectively inhibits the proliferation of tumor cells. This action is exhibited by inhibition of the mitochondrial membrane enzyme, glutaminase, of tumor cells. Therefore, the composition of the present invention is useful as an anticancer agent for treating malignant tumors associated with glutamine requirement for their proliferation. That is, it can be used for treating glutamine-requiring cancers or malignant tumors such as large intestinal cancers (e.g., colon carcinoma, rectum carcinoma), gastric cancer, prostatic cancer and hepatic cancer, for treating metastasis foci formed by distant metastasis of these tumors to organs such as the lung and liver, or for preventing distant metastasis of the tumors. The composition of the present invention is particularly effective against colon or rectum carcinomas.

The dose of the pharmaceutical composition of the present invention varies with the patient's age, weight, severity of the disease, administration route, administration frequency, etc. It is preferred that the compound (I) or a salt thereof in a daily dose of normally 0.1 to 100 mg/kg, preferably 1 to 50 mg/kg, more preferably 1 to 10 mg/kg, is administered in divided portions. The administration route may be oral or parenteral.

The following test examples, reference examples and examples further illustrate the present invention in detail but are not to be construed to limit the scope thereof.

Test Example 1

In vitro cell proliferation inhibitory activity

A cellular suspension (50 μl, 2,000 cells) of the human colon carcinoma cells WiDr or human normal fetal pulmonary fibroblasts HEL was inoculated in a 96-well microplate, and incubated at 37° C. in a 5% carbonic acid gas incubator. The next day, a 2-fold serially diluted solution (50 μl) of each compound was added and incubated for 3 days. The culture broth containing the compound was removed, the cells were washed, MTT pigment solution was added, and the surviving cell number was determined (Tada et al., J. Immunol. Methods, 93, 157–165 (1986)). The cell amount in a control group not treated with the compound solution was used as a standard (100%). The ratio of the cell amount in each treated group to that in the control group was calculated, and the $IC_{50}$ (i.e., a compound concentration required for decreasing the surviving cell amount to 50% of that in the control group) was calculated.

The results are in Table 1. Each of the test compounds did not inhibit the proliferation of the normal cells HEL, but inhibited the proliferation of the colon carcinoma cells WiDr in a low concentration.

TABLE 1

| Cell proliferation inhibitory test | | |
|---|---|---|
| | $IC_{50}$ (μg/ml) | |
| Compound | Colon carcinoma cells WiDr | Normal cells HEL |
| 2-Aminoimidazole sulfate | 12 | >80 |
| 2-Amino-1-methylimidazole hydrochloride | 1.1 | >80 |
| 2-Amino-1-ethylimidazole hydrochloride | 4.4 | >80 |
| 2-Amino-1-methylimidazoline hydrochloride | 1.4 | >80 |

TABLE 1-continued

| Cell proliferation inhibitory test | | |
|---|---|---|
| | $IC_{50}$ (μg/ml) | |
| Compound | Colon carcinoma cells WiDr | Normal cells HEL |
| N-(1-methylimidazol-2-yl)benzylideneamine (Reference Example 7) | 1.4 | >80 |
| N-(1-methylimidazol-2-yl)-4-methoxybenzylideneamine hydrochloride (Reference Example 9) | 2.2 | >80 |
| 2-Amino-1-(2-propenyl)imidazole hydrochloride (Example 1) | 4.2 | >80 |
| Methyl (2S)-2-amino-4-[(1-methylimidazol-2-yl)carbamoyl]-butyrate dihydrochloride (Example 8) | 5 | >80 |
| (2S)-2-Amino-4-[(1-methylimidazol-2-yl)carbamoyl]butyric acid (Example 9) | 5 | >80 |
| Methyl (2S)-2-amino-3-[(1-methylimidazol-2-yl)carbamoyl]propionate dihydrochloride (Example 13) | 11 | >80 | to that in the control group was calculated, and the $IC_{50}$ (i.e., a compound concentration required for decreasing the surviving cell amount to 50% of that in the control group) was calculated.

The results are in Table 2. The results show that 2-amino-1-methylimidazole hydrochloride of the present invention selectively inhibits the proliferation of the large intestinal cancer cell strains.

TABLE 2

| Cell proliferation inhibitory test | | |
|---|---|---|
| Cancer | Cell strain | $IC_{50}$ (μg/ml) |
| Breast carcinoma | MDA-MB-453 | >80 |
| Breast carcinoma | MDA-MB-231 | >80 |
| Breast carcinoma | SK-BR-3 | >80 |
| Breast carcinoma | Hs578T | 7 |
| Breast carcinoma | T-47D | 13 |
| Throat cancer | KB | >80 |
| Lung carcinoma | A549 | 20 |
| Colon carcinoma | T84 | 2.8 |
| Colon carcinoma | LoVo | 7.6 |
| Colon carcinoma | SW948 | 3.9 |
| Colon carcinoma | LS180 | 6.3 |
| Colon carcinoma | SW620 | 11 |
| Colon carcinoma | SW48 | 8.6 |
| Colon carcinoma | SW403 | 5.2 |
| Colon carcinoma | WiDr | 1.1 |

Test Example 3

In vivo colon carcinoma inhibitory activity

The human colon carcinoma cells WiDr (5,000,000 cells) were subcutaneously transplanted to a thoracic part of each of Balb/C female nude mice (7 weeks of age). On the 5th day after the transplantation, the tumor size was measured. Five mice (per group) with almost the same tumor size were used for this experiment. Each of solutions of 2-amino-1-methylimidazole hydrochloride (50 mg/kg body weight, 100 mg/kg body weight and 200 mg/kg body weight) of the present invention in physiological saline was orally administered 3 times a day for 3 days. The day following the end of the administration, the tumor size was measured. The tumor volume was calculated from the following equation:

Tumor volume=(major axis)×(minor axis)×(minor axis)×(½)

The ratio of the tumor volume in the treated group to that in a control group to which physiological saline was administered was calculated as a proliferation rate. The results are in Table 3. 2-Amino-1-methylimidazole hydrochloride of the present invention inhibited the proliferation of the human colon carcinoma cell strain WiDr transplanted to the nude mice in a concentration-dependent manner.

TABLE 3

Test for inhibitory activity against the proliferation of tumor cells transplanted to the nude mice

| Compound concentration (mg/kg) | Proliferation rate (%) |
| --- | --- |
| 0 | 100 |
| 50 | 76 |
| 100 | 64 |
| 200 | 49 |

Test Example 4

Activity of a compound having a protective group at the 2-amino group

The human colon carcinoma cells WiDr (5,000,000 cells) were subcutaneously transplanted to the thoracic parts of Balb/C female nude mice (7 weeks old). On the 5th day after the transplantation, the tumor cell size was measured. Five mice (per group) with almost the same tumor size were used for this experiment. A solution of 2-benzyloxycarbonylamino-1-methylimidazole hydrochloride (80 mg/kg body weight) of the present invention in physiological saline was orally administered 3 times a day for 3 days. The day following the end of the administration, the tumor cell size was measured. The tumor volume was calculated from the following equation:

Tumor volume=(major axis)×(minor axis)×(minor axis)×(½)

The ratio of the tumor volume in the treated group to that in a control group to which physiological saline was administered was calculated as a proliferation rate. The results are in Table 4.

The results show that 2-benzyloxycarbonylamino-1-methylimidazole hydrochloride of the present invention inhibited the proliferation of the human large intestinal cancer cell strain WiDr transplanted to nude mice.

TABLE 4

Test for inhibitory activity against the proliferation of tumor cells transplanted to nude mice

| Compound concentration (mg/kg) | Proliferation rate (%) |
| --- | --- |
| 0 | 100 |
| 80 | 70 |

Test Example 5

Inhibitory activity against the mitochondrial membrane enzyme glutaminase

1) Preparation of crude enzyme samples

The human colon carcinoma cells WiDr (wet weight: 2 g) were crushed in the buffer A (20 ml) (250 mM D-mannitol, 70 mM sucrose, 10 mM HEPES (pH 7.4)) and centrifuged at 600×g for 10 minutes. The resulting supernatant was further centrifuged at 8,000×g for 10 minutes. The resulting precipitate was washed with the buffer A and suspended in the buffer A (5000 μl) to obtain a mitochondrial fraction which was used as a crude enzyme sample.

2) Determination of enzymatic activity

Glutaminase is an enzyme that produces glutamic acid in a phosphoric acid-dependent manner using glutamine as a substrate. Radio-labelled glutamine was used as a substrate to produce radio-labelled glutamic acid. Both of them were converted to their derivatives and separated and assayed by high performance liquid chromatography to determine the enzymatic activity. That is, the crude enzyme sample was reacted with tritium-labelled glutamine (0.8 μM, Amersham) in the buffer B (50 μl) (400 mM HEPES (pH 8.0), 6 μg/ml antimycin A, 0.4 mg/ml oligomycin) in the presence of phosphoric acid (200 mM) at 37° C. for 15 minutes. The reaction was stopped by adding 1000 μl of 6% perchloric acid (Wako Pure Chemical Industries, Ltd., Japan). The reaction mixture was centrifuged to precipitate proteins. To the supernatant (100 μl) were added 1M sodium hydroxide (40 μl) and a derivative-forming reagent (100 μl) which was prepared by adding 2-mercaptoethanol (Wako Pure Chemical Industries, Ltd., Japan) and sodium borate (9 ml, pH 10.5) to a solution of a solution of o-phthalaldehyde (108 mg, Wako Pure Chemical Industries, Ltd., Japan) in methanol (1 ml). Thus, the glutamine and glutamic acid were converted to their derivatives. These derivatives were separated and determined by reversed phase high performance liquid chromatography using octadecylsilica (YMC-Pack ODS-A, YMC, Japan) as a column and using the buffer C (20 mM sodium acetate (pH 4.56):acetonitrile=93:7) as an eluent. The enzymatic activity was calculated according to the following equation:

Enzymatic activity=(b/a+b)×c wherein a is the glutamine amount, b is the glutamic acid amount, and c is the amount of glutamine added as a substrate.

The enzymatic activities in the presence of each compound were calculated, considering the enzymatic activity in a control group in which the reaction was carried out in the absence of the compound to be 100%. The $IC_{50}$ (i.e., a compound concentration required for decreasing enzymatic activity to 50% of that in the control group) was calculated.

The results are in Table 5. Each of the tested compounds inhibited mitochondrial membrane glutaminase activity of the colon carcinoma cells WiDr. The order of the strength of these activities was the same as that of the cell proliferation inhibitory activities shown in Table 1.

TABLE 5

Test for inhibitory activity against the enzymatic activity of glutaminase.

| Compound | $IC_{50}$ (mM) |
| --- | --- |
| 2-Aminoimidazole sulfate | 130 |
| 2-Amino-1-methylimidazole hydrochloride | 30 |
| 2-Amino-1-ethylimidazole hydrochloride | 50 |
| 2-Amino-1-methylimidazoline hydrochloride | 100 |

TABLE 5-continued

Test for inhibitory activity against the enzymatic activity of glutaminase.

| Compound | IC$_{50}$ (mM) |
| --- | --- |
| 2-Amino-1-(2-propenyl)imidazole hydrochloride (Example 1) | 110 |
| 3-(2-Aminoimidazol-1-yl)-L-alanine methyl ester dihydrochloride (Example 5) | 40 |
| 3-(2-Aminoimidazol-1-yl)-L-alanine dihydrochloride (Example 6) | 49 |
| Methyl (2S)-2-amino-4-[1-methyl-imidazol-2-yl)carbamoyl]butyrate dihydrochloride (Example 8) | 32 |
| (2S)-2-Amino-4-[(1-methylimidazol-2-yl) carbamoyl]butyrate (Example 9) | 36 |
| Methyl (4S)-4-amino-4-[(1-methyl-imidazol-2-yl)carbamoyl]butyrate dihydrochloride (Example 11) | 46 |
| Methyl (2S)-2-amino-3-[(1-methyl-imidazol-2-yl)carbamoyl]propionate dihydrochloride (Example 13) | 32 |
| 1-Methyl-2-(phenylalanyl)amino-imidazole dihydrochloride (Example 15) | 58 |

The results in Tables 1, 2, 3, 4 and 5 show that the compounds of the present invention exhibit excellent inhibitory activity against the enzyme glutaminase and selectively inhibit the proliferation of tumor cells.

Reference Example 1

Preparation of 2-(dimethylaminomethylene)aminoimidazole

2-Aminoimidazole sulfate (5.0 g) was dissolved in water (100 ml), sodium carbonate (6.0 g) was added, and the mixture was stirred for 30 minutes. The solvent was evaporated under reduced pressure, ethanol was added to the residue, and the insoluble materials were filtered off. The filtrate was concentrated under reduced pressure. The residue was dissolved in dimethylformamide (DMF: 20 ml), dimethylformamide dimethyl acetal (9.0 g) was added, and the mixture was stirred overnight. The solvent was evaporated under reduced pressure, and the residue was dissolved in ethyl acetate, washed with saturated brine and dried over magnesium sulfate. The solvent was evaporated under reduced pressure. The resulting crude crystals were washed with cooled ethyl acetate to give 2-(dimethylaminomethylene)aminoimidazole (3.38 g, Yield: 64%).

mp: 146°–147° C.

Elemental Analysis:

Calcd. for $C_6H_{10}N_4$: C,52.16%; H,7.29%; N,40.55%

Found: C,51.97%; H,7.08%; N,40.41%

IR (KBr)cm$^{-1}$: 1625, 1560, 1375.

$^1$H-NMR (CDCl$_3$) δ: 3.01(3H,s), 3.07(3H,s), 6.76 (2H,s), 8.48(1H,s).

Reference Example 2

Preparation of 2-(dimethylaminomethylene)amino-1-(2-propenyl)imidazole

Potassium t-butoxide (0.37 g) and 3-bromo-1-propene (0.3 ml) were added to a solution of 2-(dimethylaminomethylene)aminoimidazole (0.2 g) in DMF (3 ml) under ice-cooling. After warming to room temperature, the mixture was stirred for 30 minutes. Water was added to the reaction mixture, and the product was extracted with chloroform. The extract was dried over anhydrous magnesium sulfate, and the solvent was evaporated under reduced pressure. The resulting residue was purified by column chromatography on silica gel (eluent: chloroform-methanol-ammonia water= 40:1:0.1) to give 2-(dimethylaminomethylene)amino-1-(2-propenyl)imidazole (0.31 g, Yield: 80%) as a brown oil.

$^1$H-NMR (CDCl$_3$) δ: 3.01(3H,s), 3.05(3H,s), 4.52 (2H, dt,J=1.5 Hz,5.5 Hz), 5.11(1H,dq,J=1.5 Hz,17 Hz), 5.17 (1H,dq,J=1.5 Hz,10 Hz), 5.93(1H,ddt,J=5.5 Hz,10 Hz,17 Hz), 6.65 (1H,d,J=1.5 Hz), 6.75(1H,d,J=1.5 Hz), 8.46(1H,s).

Reference Example 3

Preparation of 2-(dimethylaminomethylene)amino-1-(2-propynyl)imidazole

According to the same manner as that in Reference Example 2, 2-(dimethylaminomethylene)amino-1-(2-propynyl)imidazole (0.27 g, Yield: 70%) was obtained as a brown oil from 2-(dimethylaminomethylene)aminoimidazole (0.3 g), potassium t-butoxide (0.37 g) and 3-bromo-1-propyne (0.25 ml).

$^1$H-NMR (CDCl$_3$) δ: 2.33(1H,t,J=2.5 Hz), 3.03(3H,s), 3.05(3H,s), 4.71(2H,d,J=2.5 Hz), 6.76(1H,d,J=2.5 Hz), 6.85(1H,d,J=2.5 Hz), 8.41(1H,s).

Reference Example 4

Preparation of 3-(2-dimethylaminomethylene-aminoimidazol-1-yl)-N-(benzyloxycarbonyl)-L-alanine methyl ester:

Under an atmosphere of argon, N-(benzyloxycarbonyl)-L-serine methyl ester (1–44 g) was dissolved in dichloromethane (28 ml), and the solution was cooled to –50° C. Diisopropylethylamine (0.812 g) and trifluoromethanesulfonic anhydride (1.77 g) were added at the same temperature, and the mixture was stirred for 1.5 hours. Hexane (28 ml) was added, and the resulting mixture was subjected to flush chromatography on silica gel (13 g) (eluent: hexanedichloromethane=1:1, 500 ml). The eluate was concentrated to a final volume of 10 ml, diluted with dichloromethane (25 ml), and then added dropwise under an atmosphere of argon to a solution of 2-(dimethylaminomethylene)aminoimidazole (718 mg) in DMF (13 ml) cooled to –20° C. After the mixture was stirred at the same temperature for 2 hours, dichloromethane (300 ml) was added, and the mixture was washed with saturated brine and dried over anhydrous magnesium sulfate. The solvent was evaporated under reduced pressure. The residue was purified by silica gel flush column chromatography (eluent: 7% ammonia-containing ethanol-chloroform=1:49) to give the title compound (975 mg).

IR (Neat) cm$^{-1}$: 3230, 3030, 2950, 1750, 1720, 1630, 1520, 1480, 1430, 1400, 1370, 1335, 1280, 1205, 1170, 1100, 1080, 1050, 1025.

$^1$H-NMR (CDCl$_3$) δ: 2.91(3H,s), 3.01(3H,s), 3.71 (3H,s), 4.30 (2H,d,J=4.6 Hz), 4.55(1H,dt,J=4.6 Hz,7.0Hz), 5.04, 5.12 (2H,ABq,J=12.0Hz), 6.54(1H,d,J=1.6 Hz), 6.68 (1H, d,J=1.6 Hz), 7.33(5H,s), 7.59(1H,d,J=7.0Hz), 8.37(1H,s).

Reference Example 5

Preparation of 3-(2-dimethylaminomethyleneaminoimidazol-1-yl)-L-alanine methyl ester:

3- (2-Dimethylaminomethyleneaminoimidazol-1 -yl)-N-(benzyloxycarbonyl)-L-alanine methyl ester (937 mg) was dissolved in methanol (25 ml), and 50% water-containing 10% Pd/C (468 mg) was added. Then, the mixture was vigorously stirred for 2 hours under an atmosphere of hydrogen. The catalyst was filtered off. The solvent was evaporated under reduced pressure. The resulting residue was purified by silica gel flush column chromatography (eluent: 7% ammonia-containing ethanol-chloroform a 3:97) to give the title compound (482 mg).

IR (Neat)cm$^{-1}$: 3370, 3300, 2950, 1730, 1630, 1520, 1480, 1460, 1430, 1395, 1365, 1280, 1250, 1200, 1170, 1100, 1070, 1025.

$^1$H-NMR (CDCl$_3$) δ: 3.02(3H,s), 3.05(3H,s), 3.72 (3H,s), 3.81 (1H,dd,J=5.0 Hz, 7a. OHz), 4.08 (1H,dd,J=7.0Hz, 13.8 Hz), 4.27(1H,dd,J=7.0Hz,13.BHz), 6.64(1H,d,J=1.6 Hz), 6.73(1H,d,J=1.6 Hz), 8.42(1H,s).

Reference Example 6

Preparation of N-(2-imidazolyl)benzylideneamine:

2-Aminoimidazole sulfate (10.0 g) was dissolved in water (70 ml), and the solution was neutralized with sodium carbonate (12.5 g, 1.5 equivalents). The solvent was evaporated, ethanol was added, and the insoluble materials were filtered off. Evaporation of the solvent in the filtrate gave a brown oil (6.2 g). 1.0 g of the oil was dissolved in ethanol (5 ml), benzaldehyde (1.28 g) was added, and the mixture was stirred at room temperature for 2 days. The solvent was evaporated, the residue was purified by silica gel column chromatography (eluent: ethyl acetate—hexane=1:1), and the solvent in the desired fraction was evaporated. The precipitated pale yellow prisms were separated by filtration using diethyl ether—hexane to give the title compound (0.88 g, 43.0%).

mp: 121.5°–123.0° C.

IR (KBr) cm$^{-1}$: 3130–2800, 1605, 1575, 1445.

$^1$H-NMR (CDCl$_3$) δ: 7.06(2H,s), 7.46–7.50(3H,m), 7.89–7.94(2H,m), 9.29(1H,s).

Reference Example 7

Preparation of N-(1-methylimidazol-2-yl)benzylideneamine:

N-(2-imidazolyl)benzylideneamine (0.2 g) was dissolved in DMF (4 ml), and potassium t-butoxide (0.15 g) and methyl iodide (0.18 g) were added. The mixture was stirred at room temperature for 3 hours. The solvent was evaporated, and water was added. The mixture was extracted with ethyl acetate. The organic layer was washed with water and saturated brine and dried over magnesium sulfate, and the solvent was evaporated. The residue was purified by silica gel column chromatography (eluent: chloroform). The resulting crude crystals were recrystallized from diethyl ether—hexane to give the title compound (0.1 g, 49.9%) as pale yellow needles.

mp: 71.0°–72.0° C.

Elemental Analysis:

Calcd. for C$_{11}$H$_{11}$N$_3$: C,71.33%; H,5.99%; N,22–69%

Found: C,71.40%; H,6.02%; N,22.62%

IR (KBr)cm$^{-1}$: 3080–2900, 1605, 1570, 1510, 1480, 760, 685.

$^1$H-NMR (CDCl$_3$) δ: 3.79(3H,s), 6.92(1H,d,J=1.2 Hz), 7.01(1H,d,J=1.2 Hz), 7.45–7.49(3Hm), 7.93–7.98(2H,m), 9.22(1H,s).

Reference Example 8

Preparation of N-(1-methylimidazol-2-yl)benzylideneamine hydrochloride:

N-(1-methylimidazol-2-yl)benzylideneamine (0.1 g) was dissolved in diethyl ether, and 4N hydrochloric acid—ethyl acetate (0.2 ml) was added. The precipitated pale yellow powder (70.mg, 21.9%) was separated by filtration.

mp: 95.0°–98.0° C.

IR (KBr)cm$^{-1}$ 3120–3050, 1665, 1620, 1585.

$^1$H-NMR (CDCl$_3$) δ: 3.83(3H,s), 6.89(1H,s), 6.95 (1H,s), 7.59–7.73(3H,m), 8.03–8.07(2H,m), 9.27(1H,s).

Reference Example 9

Preparation of N-(1-methylimidazol-2-yl)-4-methoxybenzylideneamine hydrochloride:

2-Amino-1-methylimidazole hydrochloride (0.3 g) was dissolved in ethanol (4 ml), and sodium methoxide (28% methanol solution: 0.5 ml) and p-anisaldehyde (0.34 g) were added. The mixture was heated at reflux overnight. The solvent was evaporated. The residue was purified by silica gel column chromatography (eluent: methanol-chloroform= 5:95), and the solvent in the desired fraction was evaporated. The precipitated pale yellow prisms were separated by filtration using hexane. The resulting crystals were dissolved in chloroform, and 4N hydrochloric acid—ethyl acetate (0.22 ml) was added. The solvent was evaporated, and the precipitated pale yellow was separated by filtration using diethyl ether to give the title compound (0.17 g, 26.9%).

mp: 191.0°–192.0° C.

Elemental Analysis:

Calcd. for C$_{12}$H$_{14}$N$_3$0C1·0.3H$_2$0: C,56.06%; H,5.72%; N,16.34%

Found: C,56.07%; H,5.62%; N,16.46%

IR (KBr) cm$^{-1}$: 2840–2670, 1585, 1255, 1160.

$^1$H-NMR (DMSO-d$_6$) δ: 3.80 (3H, s), 3.90 (3H, s), 7.18 (2H,d,J=8.8 Hz), 7.57(1H,d,J=2.0Hz), 7.62 (1H,d,J= 2.0Hz), 8.02 (2H,d,J=8.BHz), 9.12(1H,s).

Example 1

Preparation of 2-amino-1-(2-propenyl)imidazole hydrochloride 2-(Dimethylaminomethylene)amino-1-(2-propenyl)imidazole (0.2 g) was dissolved in 6N hydrochloric acid (5 ml), and the solution was heated under reflux for 1 hour. The solvent was evaporated under reduced pressure, and the resulting residue was dissolved in aqueous saturated sodium carbonate solution (1 ml). The solution was concentrated under reduced pressure, the organic compounds were extracted with chloroform, and the solvent was evaporated under reduced pressure. The resulting residue was purified by column chromatography on silica gel (eluent: chloroform-methanol-ammonia water=20: 1:0.1) to give 2-amino-1-(2-propenyl)imidazole. This compound was dissolved in dichloromethane, and 4N hydrochloric acid-ethyl acetate (2 ml) was added to form its hydrochloric acid salt. The salt was recrystallized from acetonitrile to give 2-amino-1-(2-propenyl)imidazole hydrochloride (0.19 g, Yield: 71%) as pale yellow needles.

mp: 98°–99° C.

$^1$H-NMR (DMSO-$d_6$) δ: 4.54(2H,dt,J=1.5 Hz,5.5 Hz), 5.10(1H,dq,J=1.5 Hz,17 Hz), 5.26(1H,dq,J=1.5 Hz,10 Hz), 5.91(1H,ddt,J=5.5 Hz,10 Hz,17 Hz), 6.94(2H,s), 7.76(2H,brs), 12.20 (1H,brs ).

Example 2

Preparation of 2-amino-1-(2-propynyl)imidazole hydrochloride

According to the same manner as that in Example 1, 2-(dimethylaminomethylene)amino-1-(2-propynyl)imidazole (0.2 g) was treated with 6N hydrochloric acid to give 2-amino-1-(2-propynyl)imidazole hydrochloride (0.12 g, Yield: 54%).

mp: 119°–120° C.

$^1$H-NMR(CDCl$_3$) δ: 3.06(1H,t,J=2.5 Hz), 4.84 (2H,d,J=2.5 Hz), 6.95(1H,d,J=2.5 Hz), 7.03(1H,d,J=2.5 Hz), 7.89(2H,brs), 12.21(1H,brs).

Example 3

Preparation of 2-ethoxycarbonylamino-1-methylimidazole hydrochloride

Ethyl chlorocarbonate (0.6 g) was added to a solution of 2-amino-1-methylimidazole hydrochloride (0.3 g) in pyridine (5 ml), and the mixture was stirred under heating at 100° C. for 2 hours. The solvent was evaporated under reduced pressure, the residue was dissolved in water, and sodium carbonate was added until the solution became alkaline. The solvent was evaporated under reduced pressure, and then the residue was purified by column chromatography on silica gel (eluent: chloroform) to give 2-ethoxycarbonylamino-1-methylimidazole. This compound was dissolved in dichloromethane, and 4N hydrochloric acid-ethyl acetate (2 ml) was added to form its hydrochloric acid salt. The resulting crude crystals were washed with ether to give 2-ethoxycarbonylamino-1-methylimidazole hydrochloride (0.29 g, Yield: 56%) as colorless prisms.

mp: 129°–131° C.

Elemental Analysis:

Calcd. for $C_7H_{12}ClN_3O_2 \cdot 0.2H_2O$: C,40.18%; H,5.97%; N,20.08%

Found: C,40.00%; H,6.40%; N,20.05%

IR (KBr)cm$^{-1}$: 3170–2990, 1745, 1640, 1250.

$^1$H-NMR (DMSO-$d_6$) δ: 1.30(3H,t,J=7.1 Hz), 3.66(3H,s), 4.28(2H,q,J=7.1 Hz), 7.32(1H,d,J=1.4 Hz), 7.43(1H,d,J=1.4 Hz).

Example 4

Preparation of 2-benzyloxycarbonylamino-1-methylimidazole hydrochloride

2-Amino-1-methylimidazole hydrochloride (0.3 g) was dissolved in 1N sodium hydroxide solution (5 ml). Benzyloxycarbonyl chloride (0.43 g) and ether (2 ml) were added, and the mixture was stirred for 1 hour. The product was extracted with ethyl acetate, the extract was washed with water and aqueous saturated sodium chloride solution and dried over magnesium sulfate, and the solvent was evaporated under reduced pressure. Diethyl ether-hexane was added to the resulting residue for crystallization, and the crystals were separated by filtration. The crystals of 2-benzyloxycarbonylamino-1-methylimidazole thus obtained was dissolved in chloroform, and 4N hydrochloric acid-ethyl acetate (0.5 ml) was added to form its hydrochloric acid salt. The crude crystals thus obtained were washed with ether to give 2-benzyloxycarbonylamino-1-methylimidazole hydrochloride (0.2 g, Yield: 30% ) as white powder.

mp: 141°–142° C.

Elemental Analysis:

Calcd. for $C_{12}H_{14}ClN_3O_2 \cdot 0.2H_2O$: C,53.12%; H,5.35%; N,15.94%

Found: C,53.17%; H,5.24%; N,15.45%

IR (KBr)cm$^{-1}$: 3070, 1740, 1625, 1250 1215.

$^1$H-NMR (DMSO-$d_6$) δ: 3.64(3H,s), 5.29(2H,s), 7.30 (1H, d, J=2.2 Hz ), 7.40–7.47(6H,m).

Example 5

Preparation of 3-(2-aminoimidazol-1-yl)-L-alanine methyl ester dihydrochloride:

3-(2-Dimethylaminomethyleneaminoimidazol-1-yl)-L-alanine methyl ester (470 mg) was suspended in 20% hydrochloric acid-methanol (40 ml), and the suspension was stirred at 55° C. for 6 days. The solvent was evaporated under reduced pressure, methanol was added to the residue, and the solvent was evaporated again. Methanol-ether was added to the residue, and the mixture was allowed to stand to precipitate colorless needles. The crystals were separated by filtration, washed with methanol followed by ether, and dried to give the title compound (292 mg).

IR (KBr) cm$^{-1}$: 3380, 3200, 3150, 3060, 2950, 2900, 2830, 2780, 2630, 1750, 1660, 1520, 1435, 1360, 1290, 1260, 1150, 1125, 1075.

$^1$H -NMR (DMSO-$d_6$) δ: 3.78(3H,s), 4.48(3H,s), 6.94 (1H,d,J=2.4 Hz), 6.98(1H,d,J=2.4 Hz), 8.01(2H,s), 9.02(2H,brs).

Example 6

Preparation of 3-(2-aminoimidazol-1-yl)-L-alanine dihydrochloride:

3-(2-Aminoimidazol-1-yl)-L-alanine methyl ester dihydrochloride (103 mg) was dissolved in 6N hydrochloric acid (4 ml), and the mixture was stirred at 55° C. for 5 days. The solvent was evaporated under reduced pressure. Methanol was added to the residue, and the insoluble materials were filtered off. Evaporation of the solvent in the filtrate gave the title compound (57 mg).

IR (KBr) cm$^{-1}$: 3360, 3150, 2970, 1740, 1660, 1535, 1500, 1450, 1260, 1120, 1090, 1040.

$^1$H-NMR (CD$_3$OD) δ: 4.42–4.60(3H,m), 6.93(2H,s).

Example 7

Preparation of methyl (2S)-2-t-butoxycarbonylamino-4-[(1-methylimidazol-2-yl)carbamoyl]butyrate:

2-Amino-1-methylimidazole hydrochloride (668 mg) and N-t-butoxycarbonyl-L-glutamic acid α-methyl ester (1.31 g) were dissolved in dry pyridine (25 ml). Phosphorous trichloride (687 mg) was added under ice-cooling, and then the mixture was stirred at room temperature for 3 hours. The precipitated materials were filtered off, and the solvent was evaporated under reduced pressure. The resulting residue was dissolved in chloroform, washed with saturated brine and dried over anhydrous magnesium sulfate. The solvent was evaporated under reduced pressure, and the residue was purified by flush column chromatography on silica gel eluent: methanol-chloroform=3:97–1:19) to give the title compound (300 mg).

IR (KBr)cm$^{-1}$: 3370, 3130, 2970, 2950, 1735, 1680, 1555, 1520, 1480, 1460, 1440, 1360, 1320, 1300, 1260, 1180, 1160, 1080, 1060.

$^1$H-NMR (DMSO-d$_6$) δ: 1.39 (9H, s), 1.60–2.10 (2H,m), 2.40(2H,t,J=7.0Hz), 3.39(3H,s), 3.63(3H,s), 3.95–4.08(1H, m), 6.73(1H,d,J=1.2 Hz), 7.03(1H,d,J=1.2 Hz), 7.29(1H,d, J=8.0Hz), 9.99(1H,s).

Example 8

Preparation of methyl (2S)-2-amino-4-[(1-methylimiazol-2-yl)carbamoyl]butyrate dihydrochloride:

Methyl (2S)-2-t-butoxycarbonylamino-4-[(1-methylimidazol-2-yl)carbamoyl]butyrate (34.1 ml) was dissolved in methanol (1 ml), and 10% hydrochloric acid/ether (1 ml) was added. The mixture was stirred at room temperature for 3 hours. The solvent was evaporated under reduced pressure, and the residue was powdered in ether. The powder was separated by filtration and dried to give the title compound (27 mg).

IR (KBr) cm$^{-1}$: 3420, 3130, 2950, 2920, 1740, 1710, 1615, 1555, 1480, 1440, 1350, 1280, 1230, 1170, 1140, 1070.

$^1$H-NMR (CD$_3$OD) δ: 2.22–2.42(2H,m), 2.93 (2H,t,J=7.2 Hz), 3.80(3H,s) 3.86(3H,s), 4.19(1H,t,J=7.2 Hz), 7.22(1H, d,J=2.2 Hz), 7.28 (1H,d,J=2.2 Hz).

Example 9

Preparation of (2S)-2-amino-4-[(1-methylimidazol-2-yl)carbamoyl]butyric acid:

Methyl (2S)-2-t-butoxycarbonylamino-4-[(1-methylimidazol-2-yl)carbamoyl]butyrate (341 mg) was dissolved in dichloromethane (5 ml), and trifluoroacetic acid (1 ml) was added. The mixture was stirred at room temperature for 2 hours. Methanol and toluene were added, and then the solvents were evaporated under reduced pressure. The resulting residue was dissolved in water (4 ml), and 1N sodium hydroxide (4 ml) was added. The mixture was stirred at room temperature for 3 hours and neutralized by adding 1N hydrochloric acid. The solvent was evaporated under reduced pressure to precipitate colorless needles. The needles were separated by filtration, washed successively with water, methanol and ether, and dried to give the title compound (72 mg).

IR (KBr) cm$^{-1}$: 3440, 3180, 3070, 2980, 1695, 1645, 1620, 1550, 1480, 1440, 1420, 1420, 1400, 1355, 1320, 1280, 1230, 1200, 1180, 1155, 1140, 1080, 1045.

$^1$H-NMR (D$_2$O) δ: 2.09–2.19(2H,m), 2.58 (2H,t,J=7.4 Hz), 3.45(3H,s), 3.74(1H,t,J=6.2 Hz), 6.84 (1H,d,J=1.6 Hz), 6.96(1H,d,J=1.6 Hz).

Example 10

Preparation of benzyl (4S)-4-t-butoxycarbonylamino-4-[(1-methylimidazol-2-yl)carbamoyl]butyrate:

According to the same procedure as in Example 7, the title compound (857 mg) was obtained from 2-amino-1-methylimidazole hydrochloride (668 mg), N-t-butoxycarbonyl-L-glutamic acid (γ-benzyl ester)(1.69 g), dry pyridine (25 ml) and phosphorus trichloride (687 mg).

IR (neat) cm$^{-1}$: 3400, 3280, 2970, 1730, 1700, 1585, 1550, 1480, 1450, 1380, 1360, 1330, 1280, 1240, 1160, 1050, 1020.

$^1$H-NMR (CDCl$_3$) δ: 1.45(9H,s), 2.00–2.60(4H,m), 3.49(3H,s), 4.23–4.46(1H,m), 5.08(2H,s), 5.62(1H,d,J=7.0Hz), 6.51(1H,d,J=2.4 Hz), 6.65(1H,d,J=2.4 Hz), 7.33(5H,s).

Example 11

Preparation of methyl (4S)-4-amino-4-[(1-methylimidazol-2-yl)carbamoyl]butyrate dihydrochloride:

Benzyl (4S)-4-t-butoxycarbonylamino-4-[(1-methylimidazol-2-yl)carbamoyl]butyrate (113 mg) was dissolved in methanol (2.7 ml), and 20% hydrochloric acid-methanol (1.8 ml) was added. The mixture was stirred at room temperature for 2 hours. The solvent was evaporated under reduced pressure. The residue was triturated in ether, separated by filtration, washed with ether, and dried to give the title compound (83 mg).

IR (KBr) cm$^{-1}$: 3420, 3280, 3030, 2950, 2850, 1725, 1690, 1625, 1565, 1540, 1490, 1430, 1380, 1340, 1280, 1200, 1140, 1100, 1070.

$^1$H-NMR (CD$_3$OD) δ: 2.29–2.43(2H,m), 2.67 (2H,t,J=7.2 Hz), 3.68(3H,s), 3.87 (3H,s), 4.51(1H,t,J=5.9 Hz), 7.31(1H, d,J=2.2 Hz), 7.3 (1H,d,J=2.2 Hz).

Example 12

Preparation of methyl (2S)-2-t-butoxycarbonylamino-3-[(1-methylimidazol-2-yl)carbamoyl]propionate:

According to the same procedure as in Example 7, the title compound (300 mg) was obtained from 2-amino-1-methylimidazole hydrochloride (1.34 g), N-t-butoxycarbonyl-L-aspartic acid (α-methyl ester) (1.24 g), dry pyridine (35 ml) and phosphorus trichloride (687 mg).

IR (KBr ) cm$^{-1}$: 3420, 2970, 1740, 1710, 1585, 1550, 1490, 1390, 1360, 1340, 1280, 1240, 1210, 1160, 1050, 1020.

$^1$H-NMR (CDCl$_3$) δ: 1.45(9H,s), 2.82(1H,dd,J=4.4 Hz,16.8 Hz), 3.11(1H,dd,J=4.4 Hz,16.8Hz), 3.50(3H,s), 3.73(3H,s),4.53–4.62(1H,m), 5.40–5.80(H,brs), 6.03(1H,d, J=8.2 Hz), 6.55(1H,d,J=2.4 Hz), 6.67(1H,d,J=2.4 Hz).

Example 13

Preparation of methyl (2S)-2-amino-3-[(1-methylimidazol-2-yl)carbamoyl]propionate dihydrochloride:

According to the same procedure as in Example 11, the title compound (220 mg) was obtained from methyl (2 S )-2-t-butoxycarbonylamino-3-[(1-methylimidazol-2-yl) carbamoyl]propionate (258 mg), methanol (7.9 ml), and 20% hydrochloric acid-methanol (5.0 ml ).

IR (KBr) cm$^{-1}$: 3430, 3120, 2920, 1745, 1710, 1620, 1550, 1480, 1440, 1370, 1300, 1250, 1180, 1140, 1090, 1070.

$^1$H-NMR (CD$_3$OD) δ: 3.40 (2H,d,J=5.6 Hz), 3.80(3H,s), 3.87 (3H,s), 4.55(1H,t,J=5.6 Hz), 7.27 (1H,d,J=2.4 Hz), 7.33 (1H,d,J=2.4 Hz).

Example 14

Preparation of 2-(N-Boc-phenylalanyl)amino-1-methylimidazole:

2-Amino-1-methylimidazole hydrochloride (0.3 g) was dissolved in water, and the solution was neutralized with sodium carbonate and concentrated to dryness. The residue was dissolved in DMF (5 ml). N-Boc-phenylalanine (1.0 g) and triethylamine (0.7 ml) were added, and then diethylphosphoryl cyanide (DEPC) (0.86 ml) was added dropwise under ice-cooling. The mixture was stirred at room temperature for 2 hours. Methanol (1 ml) and water were added, and the mixture was extracted with ethyl acetate. The organic layer was washed with water and saturated brine, and dried over magnesium sulfate, and the solvent was evaporated. The residue was purified by silica gel column chromatography (eluent: methanol-chloroform=5:95), and evaporation of the solvent in the desired fraction gave a pale brown oil (0.39 g, 45.1%).

IR (KBr) cm$^{-1}$: 3280, 3030–2940, 1700, 1600–1550, 1490, 1390–1365.

$^1$H-NMR (CDCl$_3$) δ: 1.42(9H,s), 3.16–3.23(2H,m), 3.46(3H,s), 4.52–4.57 (1H,m), 5.44(1H,d,J=8.6 Hz), 6.54(1H,d,J=2.4Hz), 6.67(1H,d,J=2.4Hz), 7.21 (5H, s).

Example 15

Preparation of 1-methyl-2-(Phenylalanyl)amino-imidazole dihydrochloride:

2-(N-Boc-phenylalanyl)amino-1-methylimidazole (0.3 g) was dissolved in conc. hydrochloric acid (10 ml), and the solution was stirred at room temperature for 30 minutes. The solvent was evaporated, and the precipitated colorless powder was separated by filtration using diethyl ether to give the title compound (0.23 g, 66.3%).

mp: 231.0°–232.0° C. (decomposition)

Elemental Analysis:

Calcd. for C$_{13}$H$_{18}$Cl$_2$N$_4$0·0.5H$_2$0: C,47.86%; H,5.87%; N,17.17%

Found: C,47.48%; H,5.79%; N,17.11%

IR (KBr)cm$^{-1}$: 3150–2850, 1705, 1625, 1500.

$^1$H-NMR (D$_2$O) δ: 3.17–3.40(2H,m), 3.43(3H,s), 4.20 (1H,t,J=6.6 Hz), 6.91(1H,d,J=2.4 Hz), 6.95(1H,d,J=2.4 Hz), 7.29–7.40(5H,m).

Example 16

| | | |
|---|---|---|
| (1) | 2-Amino-1-methylimidazole | 10.0 mg |
| (2) | Lactose | 60.0 mg |
| (3) | Corn starch | 35.0 mg |
| (4) | Gelatin | 3.0 mg |
| (5) | Magnesium stearate | 2.0 mg |

A mixture of 2-amino-1-methylimidazole (10.0 mg) and lactose (60.0 mg) and corn starch (35.0 mg) was granulated by using 10% aqueous gelatin solution (0.03 ml) containing gelatin (3.0 mg), and the granules were sifted through a 1 mm-mesh sieve. The granules were dried at 40° C. and sifted again. The granules thus obtained were mixed with magnesium stearate (2.0 mg) and compressed. The core tablets thus obtained were sugar-coated with an aqueous solution of sucrose, titanium oxide, talc and acacia. The resulting tablets were polished with yellow bees wax to give coated tablets.

Example 17

| | | |
|---|---|---|
| (1) | 2-Amino-1-methylimidazole | 10.0 mg |
| (2) | Lactose | 70.0 mg |
| (3) | Corn starch | 50.0 mg |
| (4) | Soluble starch | 7.0 mg |
| (5) | Magnesium stearate | 3.0 mg |

2-Amino-1-methylimidazole (10.0 mg) and magnesium stearate (3.0 mg) were granulated using an aqueous solution (0.07 ml) of soluble starch (7.0 mg), dried and mixed with lactose (70.0 mg) and corn starch (50.0 mg). The mixture was compressed to give tablets.

Example 18

| | | |
|---|---|---|
| (1) | 2-Amino-1-methylimidazole | 5.0 mg |
| (2) | Sodium chloride | 20.0 mg |
| (3) | Distilled water | To a total volume of 2 ml |

Distilled water was added to 2-amino-1 -methylimidazole (5.0 mg) and sodium chloride (20.0 mg) to a total volume of 2.0 ml. The solution was filtered and charged into an ampule under aseptic conditions. The ampule was sterilized and then sealed to obtain an injectable solution.

What is claimed is:

1. A compound of the formula (II):

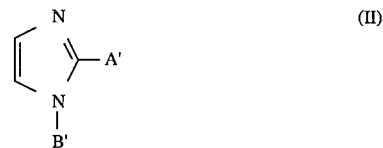

wherein A' is —NHCOOR in which R is a lower alkyl group or a benzyl group; and B' is a lower alkyl group, a lower alkenyl group or a lower alkynyl group, each of which is unsubstituted or substituted with 1 to 3 substituents selected from the group consisting of a hydroxy, amino, carboxyl, nitro, mono- or di-C$_{1-6}$ alkylamino, C$_{1-6}$ alkoxy, C$_{1-6}$ alkylcarbonyloxy and halogen; or a pharmaceutically acceptable salt thereof.

2. A compound according to claim 1, wherein B' is a lower alkyl group.

3. A compound according to claim 1, wherein B' is a straight chain or branched C$_{1-6}$ alkyl group, a straight chain or branched C$_{2-6}$ alkenyl group or a straight chain or branched C$_{2-6}$ alkynyl group, each of which is unsubstituted or substituted with 1 to 3 substituents selected from the group consisting of a hydroxy, amino, carboxyl, nitro, mono- or di-C$_{1-6}$ alkylamino, C$_{1-6}$ alkoxy, C$_{1-6}$ alkylcarbonyloxy and halogen.

4. A compound according to claim 1, wherein B' is a straight chain or branched C$_{1-6}$ alkyl group.

5. A compound according to claim 1, which is 2-benzyloxycarbonylamino-1-methylimidazole or a salt thereof.

6. A pharmaceutical composition according to claim 1, wherein the compound is 2-benzyloxycarbonylamino-1-methylimidazole.

7. A method for inhibiting glutaminase which comprises administering to a mammal in need thereof an effective amount of a compound of the formula (I):

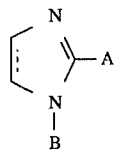

(I)

wherein A is (i) a lower alkyl group which is unsubstituted or substituted with 1 to 3 substituents selected from the group consisting of a hydroxy, amino, carboxyl, nitro, mono- or di-$C_{1-6}$ alkylamino, $C_{1-6}$ alkoxy, $C_{1-6}$ alkyl-carbonyloxy and halogen, or (ii) an amino group which is unprotected or protected with a group removable by in vivo metabolism; ==== is a single bond or a double bond, and B is (i) a hydrogen atom or (ii) a lower alkyl group, a lower alkenyl group, or a lower alkynyl group, each of which is unsubstituted or substituted with 1 to 3 substituents selected from the group consisting of a hydroxy, amino, carboxyl, nitro, mono- or di-$C_{1-6}$ alkylamino, $C_{1-6}$ alkoxy, $C_{1-6}$ alkyl-carbonyloxy and halogen, or a pharmaceutically acceptable salt thereof.

8. A method according to claim 7, wherein the glutaminase is mitochondrial glutaminase.

9. A method for treating a glutaminase-requiring cancer in a mammal which comprises administering to such a mammal in need thereof an effective amount of a compound of the formula (I):

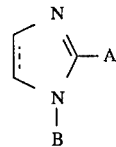

(I)

wherein A is (i) a lower alkyl group which is unsubstituted or substituted with 1 to 3 substituents selected from the group consisting of a hydroxy, amino, carboxyl, nitro, mono- or di-$C_{1-6}$ alkylamino, $C_{1-6}$ alkoxy, $C_{1-6}$ alkyl-carbonyloxy and halogen, or (ii) an amino group which is unprotected or protected with a group removable by in vivo metabolism; ==== is a single bond or a double bond, and B is (i) a hydrogen atom or (ii) a lower alkyl group, a lower alkenyl group, or a lower alkynyl group, each of which is unsubstituted or substituted with 1 to 3 substituents selected from the group consisting of a hydroxy, amino, carboxyl, nitro, mono- or di-$C_{1-6}$ alkylamino, $C_{1-6}$ alkoxy, $C_{1-6}$ alkyl-carbonyloxy and halogen, or a pharmaceutically acceptable salt thereof.

10. A method according to claim 9, wherein the glutaminase-requiring cancer is colon carcinoma.

11. A method according to claim 9, wherein the glutaminase-requiring cancer is rectum carcinoma.

12. A method according to claim 7, wherein A is an amino group which is unprotected or protected with a group removable by in vivo metabolism.

13. A method according to claim 7, wherein A is an amino group which is unprotected or protected with (i) a straight-chain or branched $C_{1-6}$ alkanoyl group which is saturated or which contains an unsaturated bond, (ii) a $C_{6-10}$ aroyl group, (iii) a $C_{1-3}$ alkylsulfonyl group, (iv) a $C_{6-10}$ arylsulfonyl group, (v) —COOR wherein R is a lower alkyl or benzyl group, (vi) —CONR$^1$R$^2$ wherein R$^1$ and R$^2$ independently are a hydrogen atom, a lower alkyl group or a $C_{6-10}$ aryl group.

14. A method according to claim 7, wherein A is amino.

15. A method according to claim 7, wherein B is a straight chain or branched $C_{1-6}$ alkyl group, a straight chain or branched $C_{2-6}$ alkenyl group or a straight chain or branched $C_{2-6}$ alkynyl group, each of which is unsubstituted or substituted with 1 to 3 substituents selected from the group consisting of a hydroxy, amino, carboxyl, nitro, mono- or di-$C_{1-6}$ alkylcarbonyloxy and halogen.

16. A method according to claim 7, wherein B is a straight chain or branched $C_{1-6}$ alkyl group.

17. A method according to claim 7, wherein ==== is a double bond.

18. A method according to claim 7, wherein the compound is 2-benzylcarbonylamino-1-methylimidazole or a pharmaceutically acceptable salt thereof.

* * * * *